(12) United States Patent
Collier et al.

(10) Patent No.: US 6,652,562 B2
(45) Date of Patent: Nov. 25, 2003

(54) SUTURE ANCHORING AND TENSIONING DEVICE

(75) Inventors: John Collier, Franklin Lakes, NJ (US); Etan S. Chatlynne, Brooklyn, NY (US); Robert Maurer, Belle Meade, NJ (US); Robert Nering, Sergeantsville, NJ (US)

(73) Assignee: Ethicon, Inc., Somerville, NJ (US)

( * ) Notice: Subject to any disclaimer, the term of this patent is extended or adjusted under 35 U.S.C. 154(b) by 131 days.

(21) Appl. No.: 10/034,636

(22) Filed: Dec. 28, 2001

(65) Prior Publication Data

US 2003/0125767 A1 Jul. 3, 2003

(51) Int. Cl.[7] ............................................. A61B 17/04
(52) U.S. Cl. .................................................... 606/232
(58) Field of Search .............................. 606/232, 151, 606/233

(56) References Cited

U.S. PATENT DOCUMENTS

| | | | |
|---|---|---|---|
| 5,078,731 A | 1/1992 | Hayhurst | |
| 5,219,359 A | * 6/1993 | McQuilkin et al. | ......... 606/232 |
| 5,376,101 A | 12/1994 | Green et al. | |
| 5,383,905 A | 1/1995 | Golds et al. | |
| 5,391,173 A | 2/1995 | Wilk | |
| 5,409,499 A | 4/1995 | Yi | |
| 5,474,572 A | 12/1995 | Hayhurst | |
| 5,514,159 A | 5/1996 | Matula et al. | |
| 5,537,776 A | 7/1996 | Gilard, Sr. | |
| 5,630,824 A | 5/1997 | Hart | |
| 5,645,553 A | 7/1997 | Kolesa et al. | |
| 5,681,351 A | 10/1997 | Jamiolkowski et al. | |
| 5,741,301 A | 4/1998 | Pagedas | |
| 5,810,853 A | * 9/1998 | Yoon | ........................... 606/151 |
| 5,849,019 A | 12/1998 | Yoon | |
| 5,919,208 A | 7/1999 | Valenti | |
| 5,976,159 A | 11/1999 | Bolduc et al. | |
| 6,001,110 A | 12/1999 | Adams | |
| 6,015,428 A | 1/2000 | Pagedas | |
| 6,039,176 A | 3/2000 | Wright | |
| 6,066,160 A | 5/2000 | Colvin et al. | |
| 6,074,409 A | 6/2000 | Goldfarb | |
| 6,106,545 A | 8/2000 | Egan | |
| 6,126,677 A | 10/2000 | Ganaja et al. | |
| RE36,974 E | * 11/2000 | Bonutti | ....................... 606/232 |
| 6,165,204 A | 12/2000 | Levinson et al. | |
| 6,200,329 B1 | 3/2001 | Fung et al. | |
| 6,293,961 B2 | 9/2001 | Schwartz et al. | |
| 6,409,743 B1 | * 6/2002 | Fenton, Jr. | ................... 606/232 |
| 6,428,550 B1 | 8/2002 | Vargas et al. | |
| 6,517,578 B2 | * 2/2003 | Hein | ....................... 623/13.13 |

FOREIGN PATENT DOCUMENTS

WO          9962406          9/1999

* cited by examiner

*Primary Examiner*—Michael J. Milano
*Assistant Examiner*—P Roberts (57) ABSTRACT

A suture anchoring and tensioning device is made from a resilient strip of polymeric or superelastic material adapted to be coiled into a tight spiral configuration that restricts movement of a suture entwined therein as the device coils about itself.

24 Claims, 7 Drawing Sheets

SUTURE ANCHORING AND TENSIONING DEVICE

FIELD OF THE INVENTION

The present invention relates to a suture anchoring and tensioning device for use with sutures in surgical procedures.

BACKGROUND OF THE INVENTION

In surgical invasive procedures sutures are commonly used to close incisions and to reunite damaged tissue. Typically, the sutures are maneuvered and passed through the affected tissue and the free ends of the sutures are individually tied together by the surgeon. In most surgical incisions, the surgical site area is sufficiently exposed to permit the surgeon to access and quickly tie the suture with a surgical knot by his or her hand. However, in other surgical procedures, such as endoscopic procedures, lapaoroscopic procedures, arthroscopic procedures and the like, the suturing site is inaccessible to the surgeon's hands. As a result, the surgeon must tie each of the suture ends into a knot at a location remote from the suturing site, and then manipulate suitably configured instruments for sliding the surgical knot to the suturing site of the incision. Conventionally, most surgical sutures are secured with surgical knots that are somewhat cumbersome and slow to tie. Further, when suturing, knot tying is one of the more time-consuming steps in the suturing process of the surgical procedure. Also, it is noted that knots are weak points in a suture. That is to say, when a knotted suture is broken from applied tension (assuming the suture is otherwise free from imperfections) the suture will break at the knot.

There remains a need for the elimination of knot tying from surgical procedures which would significantly reduce the duration of a particular surgical operation by the use of a suture anchoring and tensioning device in combination with surgical sutures. Additionally, this suture anchoring device would apply sufficient tension to the in-placed sutures in order to restrict any movement of the sutures at the surgical site. Further, the elimination of tying of surgical knots with regard to minimally invasive surgical operations is needed because of the increased difficulty and extended time involved in tying knots by the surgeon in confined surgical areas within the patient's body.

DISCUSSION OF RELATED ART

Suture locking devices such as suture clips, surgical fasteners, hinged clips, suture terminating devices, hemostatic clips, and suture fixation devices of various configurations, designs, structures and materials of construction are well known in the prior art. For example, U.S. Pat. No. 6,165,204 to Levinson, et al. discloses a shaped suture clip having a pair of plates joined together at one end to form a corner point (vertex) having an acute angle and having, at the other end, a pair of hook members, so as to clamp the suture in place. The opening of the clamp is slightly smaller than the diameter of the suture, thereby resulting in a pressure hold when the suture is passed through the suture clip. This suture clip will only clamp one end of the suture in place.

U.S. Pat. Nos. 5,474,572 and 5,645,553 disclose the use of a hinged clip that snaps closed after the suture threads are placed within the (jaws) holding members. The hinge clip is then snapped into place such that the suture is held transversely across the holding members, thus locking the suture in place. There is a possibility of not achieving a good set, as the snap may not have been properly actuated, or that the snap may have released.

U.S. Pat. No. 6,001,110 to Adams discloses a hemostatic clip having pseudoelastic properties at body temperature. The pseudoelastic NITINOL® clips are used to cause hemostatsis of blood vessels located along the gastrointestinal tract. The hemostatic clip has a first configuration that is useful for ligating blood vessels and is deformed to a second configuration to facilitate placement to a desired location within the body.

U.S. Pat. No. 6,106,545 to Egan discloses a suture tensioning and fixation device, which includes the combination of a plurality of suture retaining elements and a suture thread. The suture thread engages portions of each of the retaining elements, such that the suture thread is adapted to functionally engage the retaining elements for holding the interwoven suture segments in place for a knotless joint.

U.S. Pat. No. 6,066,160 to Colvin, et al. discloses a suture terminator device for enhanced tissue securing used in minimally invasive surgery. The suture securing device includes a pair of locking apertures for engaging a portion of a suture at its threaded end.

WO Publication No. 99/62406 to Schaller, et al. discloses a coalescent surgical clip that uses a plurality of NITINOL® spring-coiled loops to achieve the desired suturing results in an anastomosis surgical procedure. However, because the NITINOL® spring-coiled loops have a set mechanical property, the surgeon does not get the feel for the strength of the suturing in the anastomosis procedure.

In the foregoing circumstances, it is an object of the present invention to provide a suture anchoring and tensioning device that allows the surgeon to feel the amount of tension applied to the suture.

Another object of the present invention is to provide a suture anchoring device that eliminates knot tying by the surgeon performing the surgical procedure.

Yet another object of the present invention is to provide a suture anchoring device that is small so as not to interfere with adjacent suture ties.

A still further object of the present invention is to provide a suture anchoring and tensioning device that is simple to use, and would require only minimal training by the surgeon.

SUMMARY OF THE INVENTION

In accordance with the present invention, there is provided a novel suture anchoring device which overcomes the problems and shortcomings of the prior art devices discussed hereinabove. More particularly, the novel suture anchoring device includes a resilient member, which is biased into a normally coiled configuration. The resilient member is adapted to hold a suture such that the suture becomes entwined within the resilient member as the resilient member moves from an uncoiled configuration to its normally coiled configuration. The resilient member forms a tight spiral when it is in its coiled configuration, thereby tensioning the entwined suture. In one embodiment, the resilient member is made from a superelastic material, such as a nickle titanium alloy, having a memory shape. In an alternate embodiment, the resilient member is made from a polymeric plastic material having a memory shape.

BRIEF DESCRIPTION OF THE DRAWINGS

Further objects, features and advantages of the present invention will become apparent upon consideration of the following detailed description of the exemplary embodiments considered in connection with the accompanying drawings, in which.

DETAILED DESCRIPTION OF THE EXEMPLARY EMBODIMENTS

Figure 1:
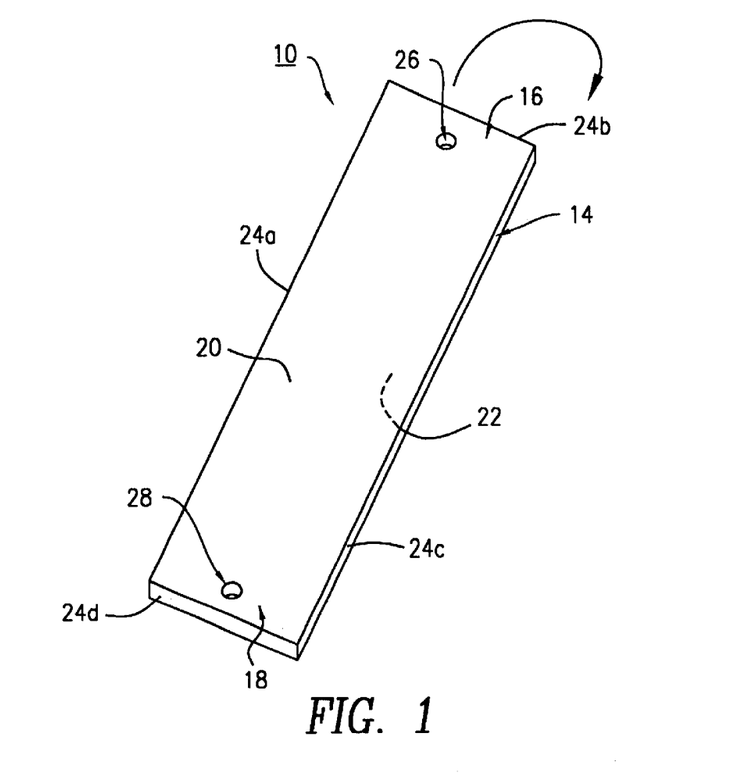
FIG. 1 is a front perspective view of a suture anchoring device constructed in accordance with a first exemplary embodiment of the present invention, the device being shown in an uncoiled configuration and without a suture.
Figure 2:
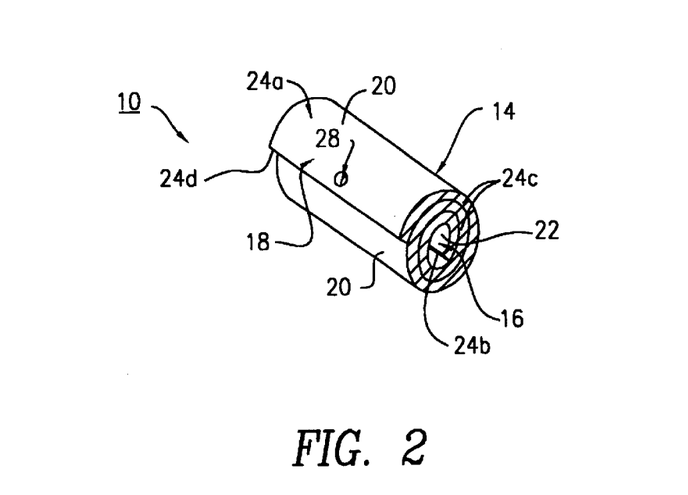
FIG. 2 is a front perspective view of the suture anchoring device of FIG. 1, the device being shown in a coiled configuration.
Figures 3A, 3B, 3C, 3D, 3E, 3F, 3G:
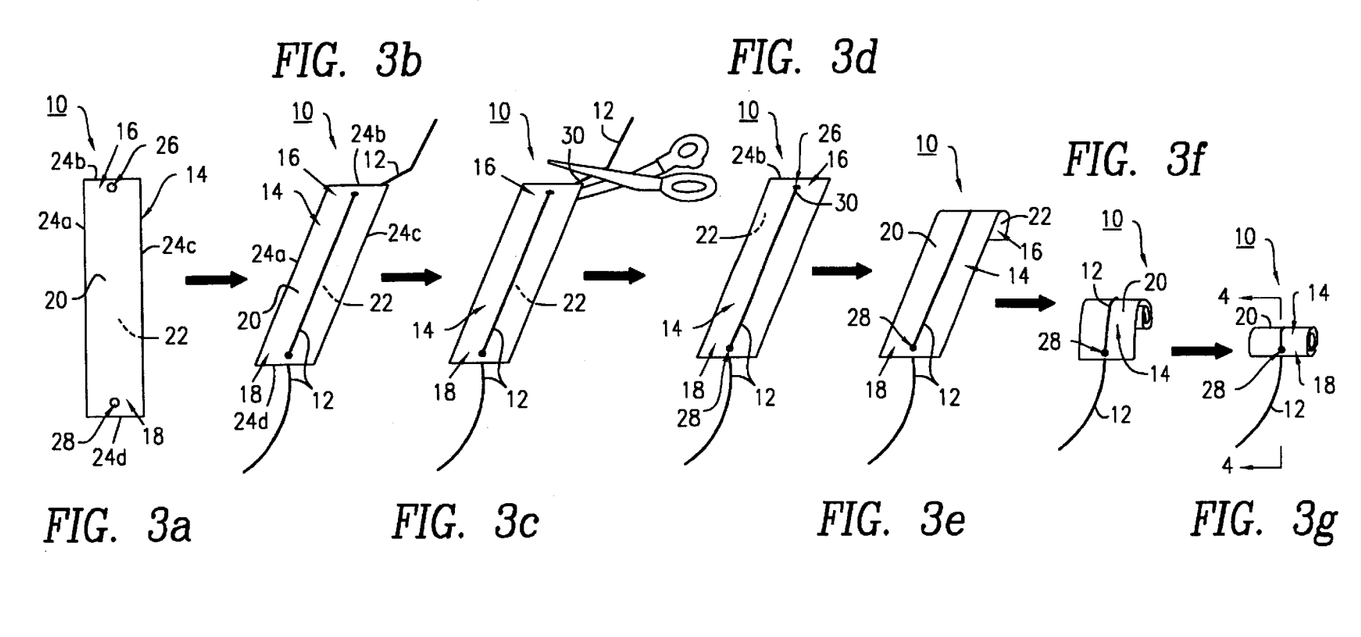
FIGS. 3a to 3g are schematic representations which illustrate the steps involved in the attachment of a suture to the suture anchoring device of FIGS. 1 and 2.
Figures 4, 5A, 5B, 5C:
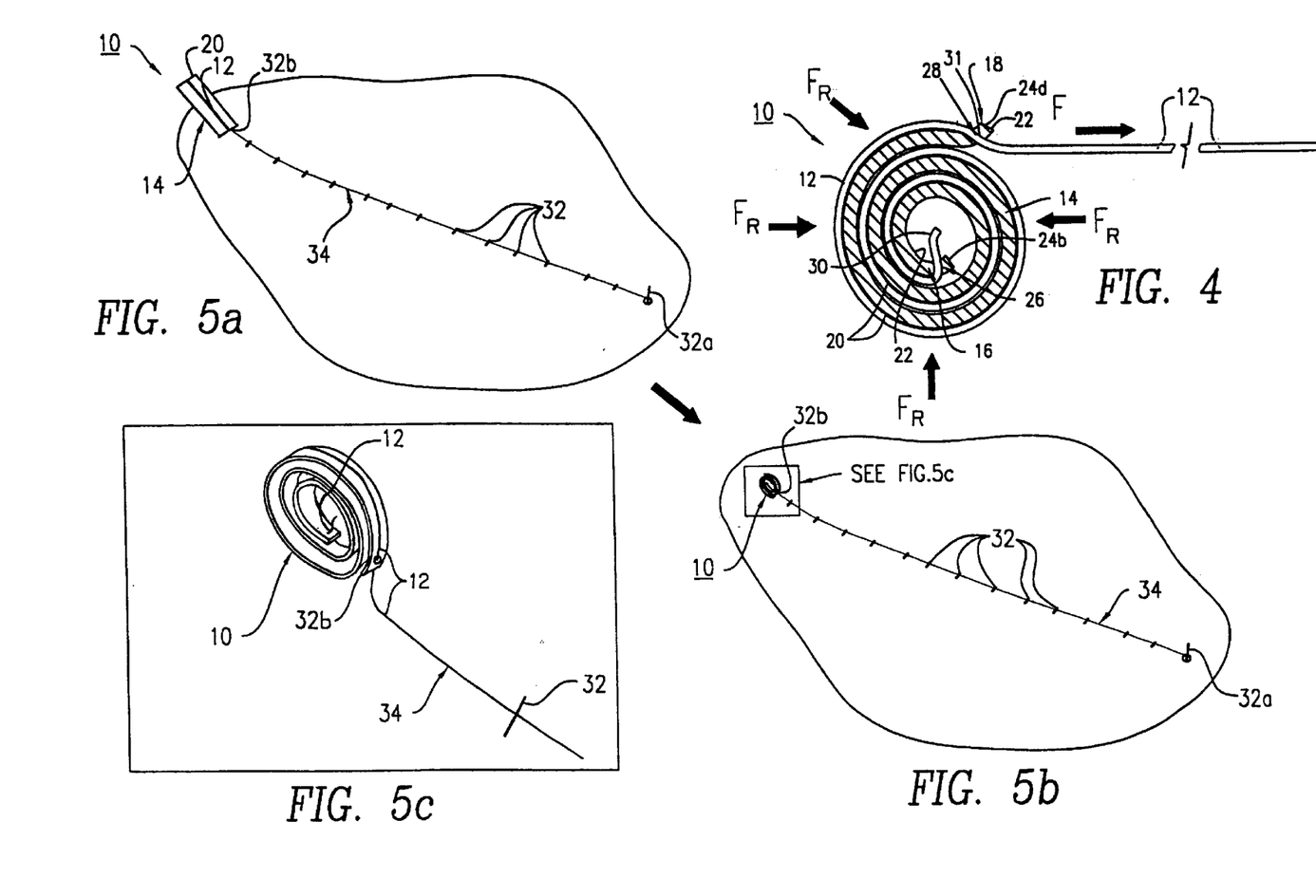
FIG. 4 is an enlarged cross-sectional view of the suture anchoring device of FIG. 3g, taken along section line 4—4 and looking in the direction of the arrows.
FIGS. 5a to 5c are schematic representations which illustrate the use of the suture anchoring device of FIGS. 1 and 2 for a wound having a running stitch.

Referring to FIGS. 1, 2, and 4, there is shown a suture anchoring and tensioning device 10 in combination with a single suture 12 for use in surgical procedures. The device 10, as shown in FIGS. 1 and 3a, includes an uncoiled, rectangularly-shaped thin planar strip 14 having a distal end 16, a proximal end 18, an outer wall 20, an inner wall 22, opposing end edges 24b, 24d and opposing side edges 24a, 24c. The uncoiled planar strip 14 also includes a first opening 26 located at the distal end 16 of strip 14 and a second opening 28 located at the proximal end 18 of strip 14. Each of the openings 26, 28 is circular in shape and is used for holding in place a portion of the suture 12, as depicted in FIG. 3b. More particularly, each of the openings 26, 28 has a diameter that is slightly larger than the suture diameter in order to prevent the inadvertent disengagement of a distal end 30 of suture 12 from the suture opening 26. The diameters are also large enough so as not to impede the surgeon from achieving a proper placement of the suture 12 within each of the openings 26, 28, as depicted in FIGS. 3b and 4. The planar strip 14 may be fabricated from any flexible, biocompatible medical material such as a polymeric or superelastic (e.g., a nickle-titanium alloy having a memory shape, such as NITINOL®,) material that can be coiled into a tight spiral configuration, as shown in FIGS. 2, 3g and 4.

If the suture anchoring and tensioning device 10 is made from a nickel-titanium alloy, such as NITINOL®, one method of manufacturing the device 10 starts with the provision of a flat rectangular strip having a width in a range of from about 1.0 mm to about 4.0 mm, a length in a range of from about 10.0 mm to about 50.0 mm and a thickness in a range of about 0.05 mm to about 0.13 mm. The flat strip is then coiled into a tight spiral configuration having a diameter in a range of from about 2.0 mm to about 4.0 mm. A fixturing/clamping device (not shown) is used to maintain the coiled configuration of the strip. The coiled strip and clamping device are then placed in a heat treatment apparatus (e.g., a furnace or salt bath) and heated to a temperature in a range of from about 450° C. to about 600° C., but preferably to a temperature in a range of from about 500° C. to about 550° C. Upon reaching the shaping and setting temperature (i.e., approximately 525° C.) the strip will become set in its coiled state. Typically, the heat treatment process lasts for a period of time in a range of from about 2 minutes to about 30 minutes, but more preferably for a period of time in a range of from about 2 minutes to about 15 minutes. The heat treated coiled strip and clamping device are then removed from the heat treating equipment. After removing the coiled strip from the clamping device, the coiled strip is quenched in water or cooled down rapidly with chilled air. To produce the device 10 depicted in FIGS. 1 and 2, the heat-treat, coiled strip would be provided with the opening 26, 28 by way of any conventional process.

FIGS. 3a through 3g demonstrate the steps involved in attaching the suture 12 to the anchoring and tensioning device 10. As shown in FIG. 3a, the device 10 may be configured into an uncoiled state from its preset coiled state by using any conventional clamping mechanism (e.g., needle holders) or a deployment device that is capable of maintaining the device 10 in its uncoiled state. Referring to FIG. 3b, the suture 12 is shown positioned along a centerline that is longitudinally aligned between the openings 26, 28 on the outer wall 20 of the uncoiled planar strip 14. With reference to FIGS. 3c to 3d, once the suture 12 is positioned on the outer wall surface 20 of the planar strip 14, excess suture 12 is trimmed away at its distal end 30 by a cutting device (e.g., scissors) prior to the coiling of the planar strip 14. This trimming could also occur following the coiling of the planar strip 14 as shown in FIGS. 3f or 3g.

Referring now to FIGS. 3e and 4, the distal end 30 of suture 12 is positioned within the opening 26 such that the distal end 30 is adjacent to and in contact with the inner wall 22 of the planar strip 14 at its distal end 16. Additionally, a short section 31 (see FIG. 4) of suture 12 is positioned within the opening 28 such that this short section 31 is adjacent to and in contact with the inner wall 22 of the planar strip 14 at its proximal end 18. It is noted that the opening 28 maintains alignment of the suture 12 and prohibits the outermost coil of the suture from slipping off the device 10, as depicted in FIG. 3g. As depicted in FIG. 3e, the initial coiling of planar strip 14 and suture 12 starts at the distal end 16 of planar strip 14. The suture 12 now becomes concomitantly entwined within the coiled strip 14 (see FIGS. 3e through 3g and 4) as the planar strip 14 is allowed to revert to its set shape, as shown in FIGS. 2, 3g and 4. Due to the nature of the entwinement, the strength of the suture 12 is not significantly compromised (as is the case when the suture is secured with a knot).

Referring again to FIGS. 3g and 4, device 10 is in a coiled configuration and the suture 12 is fully entwined within the coiled outer wall surface 20 (see FIG. 4). Configured thusly, any force (F) that is applied to suture 12 results in distributing reactive forces ($F_R$) throughout the device that are directed radially inward as shown in FIG. 4. Because empty space exists within the center of the device, the reactive forces ($F_R$) cause the device to constrict into a spiral of increased compactness thereby increasing the normal forces between the device and the suture. Because the static friction forces that hold the suture within the devices are directly proportional to these normal forces, any force that is applied to the suture further restricts movement of the suture 12 when the device 10 is appropriately positioned by the surgeon after the surgical procedure is completed.

In operation, the suture anchoring and tensioning device 10 in combination with the suture 12 may be used in various surgical procedures as depicted in FIGS. 5a to 5c, 6a to 6c and 7a to 7c. For example, the suture anchoring and tensioning device 10 of the present invention may be used to secure a single suture 12, such as in surgical procedures involving a running stitch 32 on a wound or an incision site 34 where a beginning stitch 32a and an end stitch point 32b are at different locations, as shown FIGS. 5a to 5c. With reference to FIG. 5a, the suture 12 is shown inserted and positioned on the outer wall 20 of the uncoiled planar strip 14 prior to the coiling and tensioning of the suture anchoring device 10 at the end stitch point 32b. Referring now to FIGS. 5b and 5c, the coiled suture anchoring and tensioning device 10 is shown positioned at the end stitch point 32b, such that the running stitch 32 is in a tensioned condition within the wound site 34.

Figure 6A:
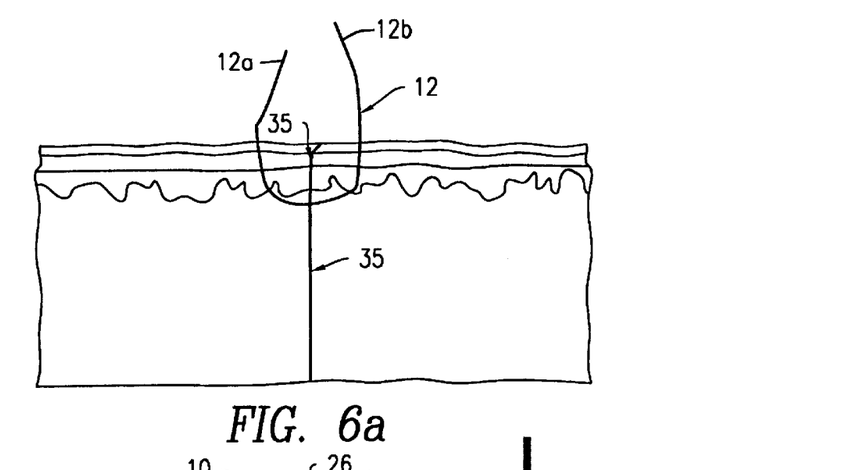
FIGS. 6a to 6c are schematic representations which illustrate the use of the suture anchoring device of FIGS. 1 and 2 for suturing an incision by a surgeon.
Figure 6B:
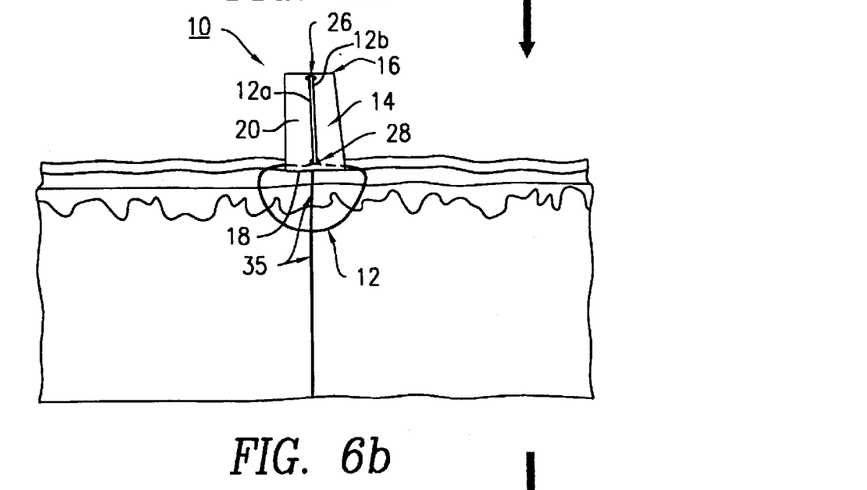
Figure 6C:
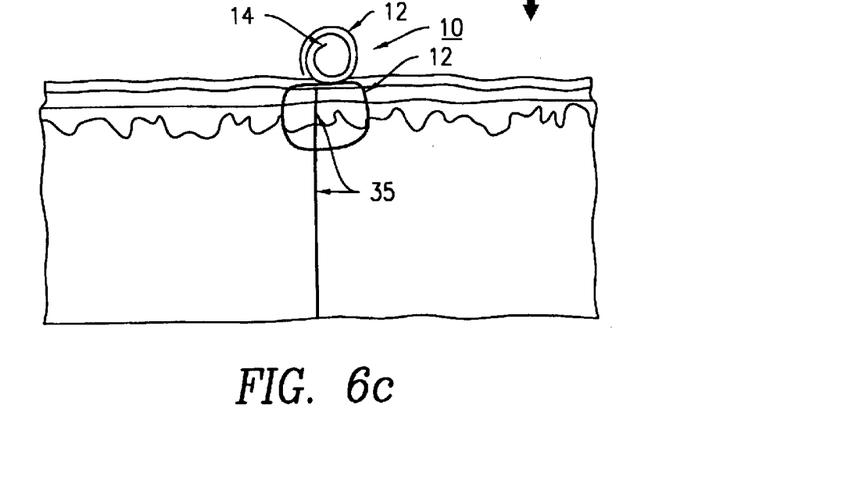

As illustrated in FIGS. 6a to 6c, the suture anchoring and tensioning device 10 is used to secure two suture end sections 12a and 12b at an incision site 35. Referring to FIG. 6b, each of the suture end sections 12a and 12b is received through the openings 28, 26, respectively, of the uncoiled planar strip 14, such that the suture end sections 12a and 12b are centered and positioned on the outer wall 20 of the uncoiled planar strip 14 prior to the coiling and tensioning of the device 10 over the incision site 35. As depicted in FIG. 6c, the device 10 is in its coiled configuration, wherein the suture end sections 12a and 12b are in a tensioned condition over the incision site 35 in order to properly close the incision.

Figures 7A, 7B, 7C:
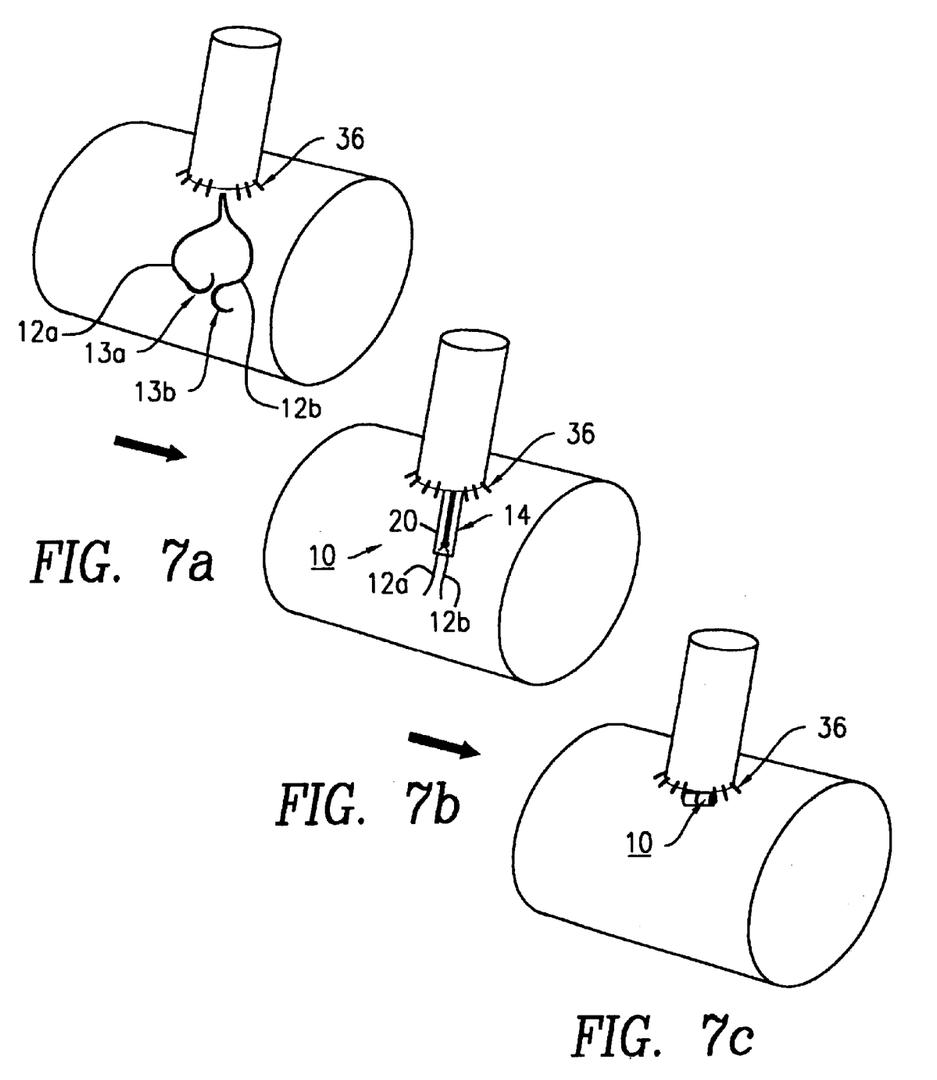
FIGS. 7a to 7c are schematic representations which illustrate the use of the suture anchoring device of FIGS. 1 and 2 for an anastomosis procedure by a surgeon.

Referring now to FIGS. 7a to 7c, the suture anchoring and tensioning device 10 is used to perform an anastomosis procedure (the interconnection/surgical joining of one tubular organ to another, for example, between blood vessels, nerves, veins, etc.) by a surgeon using double-armed suture and needle members 13a and 13b at the tubular organ (surgical) site 36 (see FIG. 7a). FIGS. 7a and 7b show the completion of the anastomosis suturing procedure by the surgeon. As previously described, the device 10 is placed in its uncoiled configuration at the desired location of fixation on the surgical site 36, wherein the needle members 13a and 13b are removed, leaving the suture end sections 12a and 12b (for two sutures) to be received within the uncoiled planar strip 14 (see FIG. 7b). Referring to FIG. 7b, the suture end sections 12a and 12b are received in the openings 28, 26, respectively, of the uncoiled planar strip 14, such that the suture end sections 12a and 12b are centered (along a longitudinal axis) and positioned on the outer wall 20 of the uncoiled planar strip 14 prior to the coiling and tensioning of the device 10 at the surgical site 36. Referring now to FIG. 7c, the device 10 is shown in its coiled configuration, wherein the suture end sections 12a and 12b are in a tensioned condition at the desired location on surgical site 36. The deployment of the device 10 (as previously described) by the surgeon for completing the anastomosis surgical procedure is such that this procedure negates the tying of a time consuming multi-throw knot.

Figure 8:
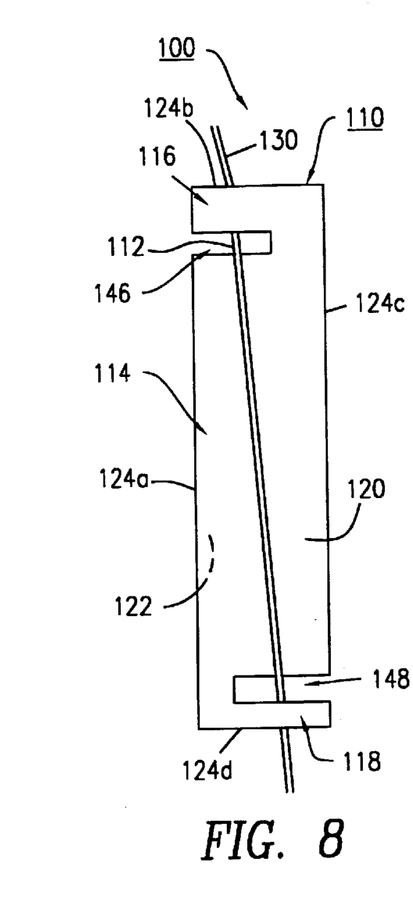
FIG. 8 is a front elevational view of a suture anchoring device constructed in accordance with a second exemplary embodiment of the present invention.

A second exemplary embodiment of the present invention is illustrated in FIG. 8. Elements illustrated in FIG. 8 which correspond to the elements described above with reference to FIGS. 1, 3g and 4 have been designated by corresponding reference members increased by one hundred. The second embodiment 100 is constructed and operates in the same manner as the first embodiment 10, unless it is otherwise stated.

With reference to FIG. 8, the uncoiled planar strip 114 of the suture anchoring device 110 does not include the openings 26, 28 which are employed by the first embodiment 10. Rather, the uncoiled planar strip 114 includes a first lateral slot 146 formed in the side edge 124a of planar strip 114 adjacent to the distal end 116 thereof and a second lateral slot 148 formed in the side edge 124c of planar strip 114 adjacent to the proximal end 118 thereof. Each of the slots 146, 148 is substantially rectangularly-shaped and is adapted to hold in place a portion of a suture 112 which extends along a centerline of an outer wall 120 of the planar strip 114 (i.e., along a central longitudinal axis thereof).

Figure 9:
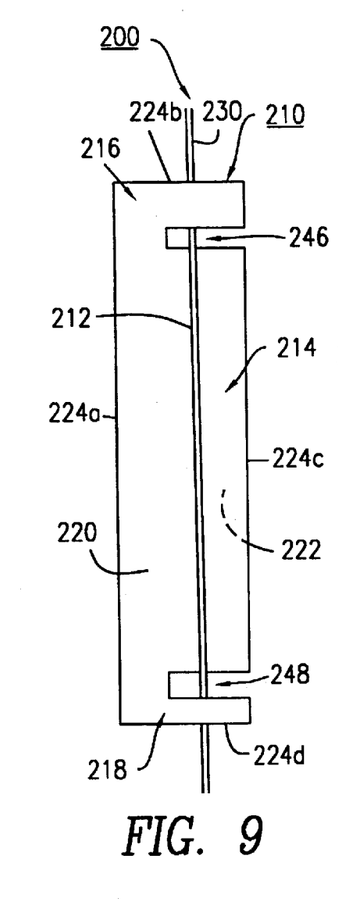
FIG. 9 is a front elevational view of a suture anchoring device constructed in accordance with a third exemplary embodiment of the present invention.

A third exemplary embodiment 200 of the present invention is illustrated in FIG. 9. Elements illustrated in FIG. 9 which correspond to the elements described above with reference to FIGS. 1, 3g and 4 have been designated by corresponding reference numbers increased by two hundred. The third embodiment 200 is constructed and operates in the same manner as the first embodiment 10, unless it is otherwise stated.

With reference to FIG. 9, the uncoiled planar strip 214 of the suture anchoring device 210 is exactly the same as the suture anchoring device 110, except that the slot 246 is formed in side edge 224c, rather than the side edge 224a. Thus, both of the slots 246, 248 are formed on the same side of the planar strip 214 (i.e., they are both formed in the side edge 224c), as shown in FIG. 9. All of the other component elements of the third embodiment 200 are exactly the same as those of the second embodiment 100.

Figure 10:
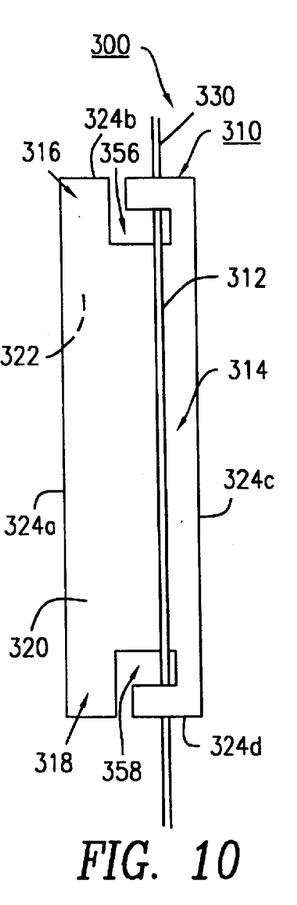
FIG. 10 is a front elevational view of a suture anchoring device constructed in accordance with a fourth exemplary embodiment of the present invention.

A fourth exemplary embodiment 300 of the present invention is illustrated in FIG. 10. Elements illustrated in FIG. 10 which correspond to the elements described above with reference to FIGS. 1, 3g and 4 have been designated by corresponding reference numbers increased by three hundred. The fourth embodiment 300 is constructed and operates in the same manner as the first embodiment 10, unless it is otherwise stated.

With reference to FIG. 10, the uncoiled planar strip 314 of the suture anchoring device 310 does not include the openings 26, 28 which are employed by the first embodiment 10. Rather, the uncoiled planar strip 314 includes a first L-shaped slot 356 formed in the end edge 324b of planar strip 314 adjacent to the distal end 316 thereof and a second L-shaped slot 358 formed in the end edge 324d of planar strip 314 adjacent to the proximal end 318 thereof. Each of the slots 356, 358 is adapted to hold in place a portion of a suture 312 which extends along an outer wall 320 of the planar strip 312 (i.e., along an off-centered longitudinal axis adjacent to the side edge 324c of the uncoiled planar strip 314).

Figure 11:
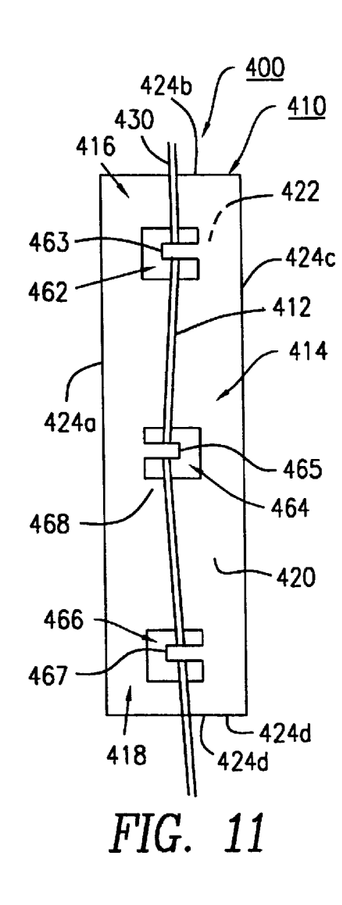
FIG. 11 is a front elevational view of a suture anchoring device constructed in accordance with a fifth exemplary embodiment of the present invention.

A fifth exemplary embodiment 400 of the present invention is illustrated in FIG. 11. Elements illustrated in FIG. 11 which correspond to the elements described above with reference to FIGS. 1, 3g and 4 have been designated by corresponding reference numbers increased by four hundred. The fifth embodiment 400 is constructed and operates in the same manner as the first embodiment 10, unless it is otherwise stated.

With reference to FIG. 11, the uncoiled planar strip 414 of the suture anchoring device 410 does not include the openings 26, 28 which are employed by the first embodiment 10. Rather, the uncoiled planar strip 414 includes a first U-shaped opening 462 having a holding tab 463 integrally attached thereto, a second U-shaped opening 464 having a holding tab 465 integrally attached thereto, and a third U-shaped opening 466 having a holding tab 467 integrally attached thereto. The U-shaped openings 462, 466 are positioned adjacent to the distal and proximal ends 416, 418, respectively of the planar strip 414, while the U-shaped opening 464 is positioned in a central region 468 intermediate to the distal end and proximal ends 416, 418. The U-shaped opening 464 faces in an opposite direction to that of the U-shaped openings 462 and 466, as shown in FIG. 11. Further, each of the center tabs 463, 465 and 467 are longitudinally aligned and are adapted to hold in place a small portion of the suture 412, such that the suture 412 remains nominally on an inner wall 422 of the planar strip 414, while the major portion of the suture 412 is on an outer wall 420, extending along a central longitudinal axis of the uncoiled planar strip 414.

Figure 12:
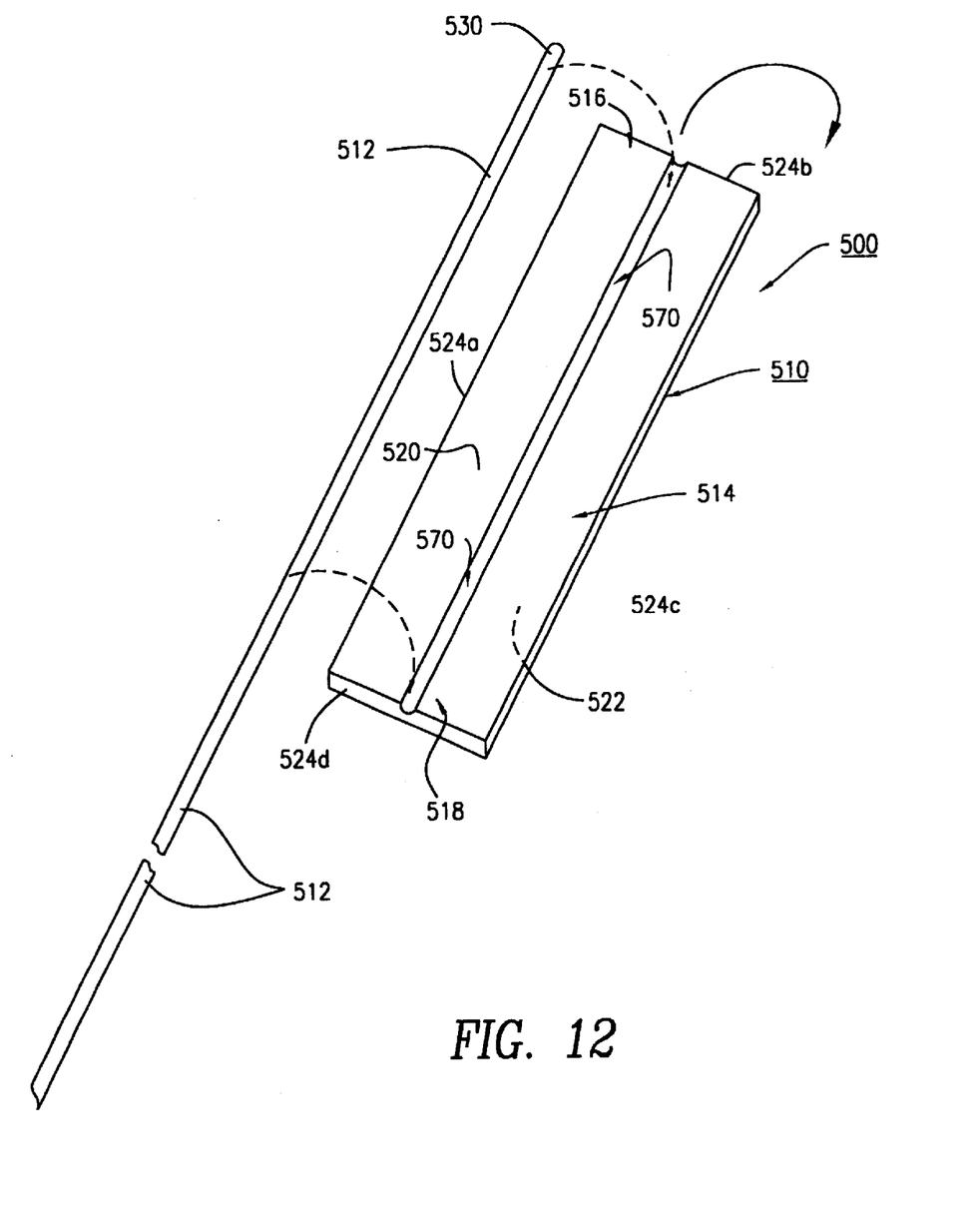
FIG. 12 is a front perspective view of a suture anchoring device constructed in accordance with a sixth exemplary embodiment of the present invention.

A sixth exemplary embodiment 500 of the present invention is illustrated in FIG. 12. Elements illustrated in FIG. 12 which correspond to the elements described above with reference to FIGS. 1, 2 and 4 have been designated by corresponding reference numbers increased by five hundred. The sixth embodiment 500 is constructed and operates in the same manner as the first embodiment 10, unless it is otherwise stated.

With reference to FIG. 12, the uncoiled planar strip 514 of the suture anchoring and tensioning device 510 does not include the openings 26, 28 which are employed by the first embodiment 10. Rather, the uncoiled planar strip 514 includes a shallow groove 570 adapted to a portion of suture 512 therein. The shallow groove 570 is centrally positioned (i.e., it runs along a longitudinal axis) on an outer wall 520 of the planar strip 514. The groove 570 may include an adhesive coating for increased adherence of the suture 512.

It should be understood that the embodiments described herein are merely exemplary and that a person skilled in the art may make many variations and modifications without departing from the spirit and scope of the present invention. For instance, there are numerous adaptations and configurations for the suture openings/guides, all of which would not change the function of the suture anchoring device of the present invention. All such variations and modifications, including those discussed above, are intended to be included within the scope of the invention as defined in the appended claims.

What is claimed is:

1. A suture anchoring device for use with a suture in a surgical procedure, comprising a resilient member having a coiled configuration, said resilient member being biased towards said coiled configuration from an uncoiled configuration, and said resilient member including holding means for holding a suture such that it becomes entwined within said resilient member as said resilient member moves from its said uncoiled configuration to its said coiled configuration.

2. A suture anchoring device in accordance with claim 1, wherein said resilient member is made from a polymeric plastic material having a memory shape.

3. A suture anchoring device in accordance with claim 1, wherein said resilient member is made from a superelastic material having a memory shape.

4. A suture anchoring device in accordance with claim 3, wherein said resilient member is made from a nickle-titanium alloy having a memory shape.

5. A suture anchoring device in accordance with claim 1, wherein said resilient member forms a tight spiral when said resilient member is in its said coiled configuration.

6. A suture anchoring device in accordance with claim 5, wherein said resilient member is a rectangularly-shaped thin planar strip when in its said uncoiled configuration.

7. A suture anchoring device in accordance with claim 6, wherein said planar strip includes a distal end, a proximal end, a pair of opposed planar surfaces, a pair of opposed end edges and a pair of opposed side edges.

8. A suture anchoring device in accordance with claim 7, wherein said distal end of said planar strip becomes an interior end of said spiral and said proximate end of said planar strip becomes an exterior end of said spiral, when said resilient member is in its said coiled configuration.

9. A suture anchoring device in accordance with claim 8, wherein one of said planar surfaces forms a spiralling outer wall and the other of said planar surfaces forms a spiralling inner wall, when said resilient member moves from its said uncoiled configuration to its said coiled configuration.

10. A suture anchoring device in accordance with claim 9, wherein a suture extending along said one planar surface is spiralled between said outer and inner walls, when said resilient member moves from its said uncoiled configuration to its said coiled configuration.

11. A suture anchoring device in accordance with claim 10, wherein said holding means prevents a spiralled suture from unspiralling, when said resilient member is in its said coiled configuration.

12. A suture anchoring device in accordance with claim 7, wherein said holding means includes a pair of openings, one of said openings being positioned proximate to one of said end edges of said planar strip, and the other of said openings being positioned proximate to the other of said end edges of said planar strip, each of said openings extending through said planar strip and being sized and shaped to receive a portion of a suture therein.

13. A suture anchoring device in accordance with claim 12, wherein each of said openings has a generally circular shape.

14. A suture anchoring device in accordance with claim 12, wherein said holding means further includes another opening extending through said planar strip and being positioned between said one opening and said other opening.

15. A suture anchoring device in accordance with claim 14, wherein each of said openings is generally U-shaped to thereby form a tab which is sized and shaped to hold a small portion of a suture passing thereunder.

16. A suture anchoring device in accordance with claim 7, wherein said holding means includes a pair of slots, one of said slots being formed in one of said side edges, and being positioned proximate to said distal end of said planar strip, and the other of said slots being formed in the other of said side edges and being positioned proximate to said proximal end of said planar strip, each of said slots being sized and shaped to receive a portion of a suture therein.

17. A suture anchoring device in accordance with claim 16, wherein each of said slots has a generally rectangular shape.

18. A suture anchoring device in accordance with claim 7, wherein said holding means includes a pair of slots, one of said slots being formed in one of said side edges and being positioned proximate to said distal end of said planar strip, and the other of said slots being formed in said side edge and being positioned proximate to said proximal end of said planar strip, each of said slots being sized and shaped to receive a portion of a suture therein.

19. A suture anchoring device in accordance with claim 18, wherein each of said slots has a generally rectangular shape.

20. A suture anchoring device in accordance with claim 7, wherein said holding means includes a pair of slots, one of said slots being formed in one of said end edges of said planar strip, and the other of said slots being formed in the other of said end edges of said planar strip, each of said slots being sized and shaped to receive a portion of a suture therein.

21. A suture anchoring device in accordance with claim 20, wherein each of said slots is generally L-shaped.

22. A suture anchoring device in accordance with claim 7, wherein said holding means includes a groove formed in said outer wall centrally positioned along and extending from one of said end edges of said planar strip to the other of said end edges of said planar strip, said groove being sized and shaped to receive a portion of a suture therein.

23. A suture anchoring device in accordance with claim 5, wherein said resilient member tensions an entwined suture when said resilient member is in it said coiled configuration.

24. A suture anchoring device in accordance with claim 1, wherein said holding means holds a pair of sutures.

* * * * *